US011255831B2

(12) United States Patent
Gerber et al.

(10) Patent No.: US 11,255,831 B2
(45) Date of Patent: Feb. 22, 2022

(54) COLORIMETRIC GAS DETECTION

(71) Applicant: Medtronic, Inc., Minneapolis, MN (US)

(72) Inventors: Martin T. Gerber, Maple Grove, MN (US); David B. Lura, Maple Grove, MN (US); Shawn Kelley, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 521 days.

(21) Appl. No.: 15/677,645

(22) Filed: Aug. 15, 2017

(65) Prior Publication Data

US 2018/0074028 A1     Mar. 15, 2018

Related U.S. Application Data (60) Provisional application No. 62/385,949, filed on Sep. 9, 2016.

(51) Int. Cl.
| | |
|---|---|
| *G01N 31/22* | (2006.01) |
| *G01N 21/78* | (2006.01) |
| *G01N 33/00* | (2006.01) |
| *A61B 5/08* | (2006.01) |
| *G01N 1/22* | (2006.01) |
| *G01N 21/75* | (2006.01) |

(52) U.S. Cl.
CPC ............ *G01N 31/223* (2013.01); *A61B 5/08* (2013.01); *G01N 1/22* (2013.01); *G01N 21/783* (2013.01); *G01N 33/0054* (2013.01); *G01N 2021/755* (2013.01)

(58) Field of Classification Search
CPC ......... G01N 33/0054; G01N 2021/755; G01N 31/223
See application file for complete search history.

(56) References Cited

U.S. PATENT DOCUMENTS

| | | | |
|---|---|---|---|
| 3,754,867 A | 8/1973 | Guenther | |
| 4,661,246 A | 4/1987 | Ash | |
| 4,772,560 A | 9/1988 | Attar | |
| 5,057,436 A * | 10/1991 | Ball | G01N 33/0031 |
| | | | 436/113 |
| 5,091,642 A | 2/1992 | Chow | |

(Continued)

FOREIGN PATENT DOCUMENTS

| | | |
|---|---|---|
| CN | 101400997 | 1/2009 |
| CN | 101482572 | 7/2009 |

(Continued)

OTHER PUBLICATIONS

European Search Report for App. No. 17190053.3, dated Jan. 2, 2018.

(Continued)

*Primary Examiner* — Jonathan M Hurst (57) ABSTRACT

The invention relates to a colorimetric gas detector for determining and monitoring gaseous substances. The colorimetric gas detector can be used in any application requiring the detection of substances in a gaseous environment. The colorimetric gas detector has a photodetector, a light source positioned opposite to the photodetector, and a receiving slot for positioning a colorimetric media between the camera and the light source.

27 Claims, 6 Drawing Sheets

(56) References Cited

U.S. PATENT DOCUMENTS

| | | | | |
|---|---|---|---|---|
| 6,244,096 | B1* | 6/2001 | Lewis | A61B 5/00 422/78 |
| 8,021,308 | B2* | 9/2011 | Carlson | A61B 5/083 600/532 |
| 10,278,617 | B1* | 5/2019 | Satterfield | A61B 5/082 |
| 2001/0048637 | A1 | 12/2001 | Weigl | |
| 2003/0113931 | A1 | 6/2003 | Pan | |
| 2005/0214863 | A1 | 9/2005 | McDevitt | |
| 2005/0265895 | A1 | 12/2005 | Kopelman | |
| 2007/0161113 | A1 | 7/2007 | Ash | |
| 2008/0200866 | A1 | 8/2008 | Prisco | |
| 2010/0061892 | A1 | 3/2010 | Flaim | |
| 2011/0081728 | A1 | 4/2011 | Putnam | |
| 2012/0135396 | A1 | 5/2012 | McDevitt | |
| 2014/0216250 | A1 | 8/2014 | Meyer | |
| 2014/0276100 | A1* | 9/2014 | Satterfield | A61B 5/082 600/476 |
| 2014/0314625 | A1 | 10/2014 | Clift | |
| 2016/0109421 | A1* | 4/2016 | Bluchel | G01N 33/0054 73/31.05 |
| 2016/0150995 | A1* | 6/2016 | Ratto | A61B 5/082 600/532 |
| 2016/0334339 | A1* | 11/2016 | Dasgupta | G01N 21/783 |

FOREIGN PATENT DOCUMENTS

| | | |
|---|---|---|
| CN | 202048893 | 3/2011 |
| CN | 103439230 A | 9/2013 |
| CN | 103803479 | 5/2014 |
| CN | 105115921 | 12/2015 |
| CN | 106124491 | 11/2016 |
| CN | 101644667 | 2/2020 |
| WO | WO 1998054563 | 12/1998 |
| WO | WO 20140121161 | 8/2014 |
| WO | WO 20150159280 | 10/2015 |

OTHER PUBLICATIONS

European Search Report for App. No. 17190066, dated Jan. 16, 2018.
European Search Report for App. No. 17190084, dated Feb. 9, 2018.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
European Office Action for App. No. 17190053.3, dated Sep. 18, 2019.
European Search Report for App. No. 17190081.4, dated Sep. 16, 2019.
Schmitt, et al, "Colorimetric Gas Sensing with Enhanced Sensitivity," Procedia Engineering, vol. 168, Sep. 3, 2016, pp. 1237-1240.
Chinese Office Action for App. No. 201710779964.4, dated Apr. 14, 2020.
Chinese Office Action for App. No. 201710779349.3, dated Jun. 1, 2020.
Chinese Office Action for App. No. 201710779964.4, dated Aug. 26, 2020.
Chinese Office Action for App. No. 201710778666.3, dated Jul. 15, 2020.
"Resources, environment and sustainable development of agriculture," edited by Liu Zhaopu, China Agricultural Science and Technology Press, pp. 209-211, Aug. 31, 1994.
"Rural Medical and Health Handbook," written by Shanghai "Rural Medical and Health Handbook Writing team, Shanghai Science and Technology Press, Jun. 1968, p. 435.
"Surface water environmental quality standard non-ionic ammonia conversion method," Teng Enjiang, et al, "China Environmental Monitoring," vol. 11, No. 4, pp. 7-9, Dec. 31, 1995.
Chinese Office Action for App. No. 201710778666.3, dated Nov. 20, 2020.

* cited by examiner

COLORIMETRIC GAS DETECTION

CROSS-REFERENCE TO RELATED APPLICATIONS

This application claims the benefit of and priority to U.S. Provisional Patent Application No. 62/385,949 filed Sep. 9, 2016, the entire disclosure of which is incorporated by reference herein.

FIELD OF THE INVENTION

The invention relates to a colorimetric gas detector for determining and monitoring gaseous substances. The colorimetric gas detector can be used in any application requiring the detection of substances in a gaseous environment. The colorimetric gas detector has a photodetector, a light source positioned opposite to the photodetector, and a receiving slot for positioning a colorimetric media between the camera and the light source.

BACKGROUND

The detection of substances in a gaseous environment is critical in several fields, including automotive, medical, environmental, or chemical fields. Known gas sensors rely on changes in conductivity of materials such as metal oxides, or changes due to catalytic reaction of the substances of interest. These systems suffer from poor selectivity, high noise, and slow reactions.

Hence, there is a need for a colorimetric gas sensor that can quickly and accurately determine specific substances in a gaseous environment. There is a further need for a gas sensor that can determine the concentration of gaseous substances in an environment based on an observable change of a colorimetric media.

SUMMARY OF THE INVENTION

The first aspect of the invention is drawn to a colorimetric gas detector. In any embodiment, the colorimetric gas detector can include a receiving slot for a colorimetric media reactable with a gas, the receiving slot positioned in a sensing chamber in fluid connection with at least one fluid inlet and at least one fluid outlet; the at least one fluid inlet and at least one fluid outlet in fluid communication with the receiving slot; a light source positioned one a first side of the receiving slot transmitting light through the receiving slot; a photodetector positioned on a second side of the receiving slot receiving the transmitted light; and a processor in electronic communication with the photodetector, the processor quantitating a detected reaction of the colorimetric media positioned in the receiving slot from an image captured by the photodetector using a reaction detection and processing algorithm.

In any embodiment, the colorimetric gas detector can include a first transparent surface positioned between the light source and the receiving slot and a second transparent surface positioned between the photodetector and the receiving slot.

In any embodiment, the first side and second side of the receiving slot can be on opposite sides of the colorimetric gas detector.

In any embodiment, the colorimetric gas detector can include a fan positioned in the fluid inlet or fluid outlet.

In any embodiment, a first light guide can direct light from the light source to the first side of the receiving slot and a second light guide can direct light received on the second side of the receiving slot directing light to the camera or photodetector.

In any embodiment, the fluid inlet and fluid outlet can both be positioned on a first side of the sensing chamber.

In any embodiment, a curved flow path can define a fluid flow path from any inlet to any outlet.

In any embodiment, the colorimetric media can be positioned in a sensor card having one or more sensing membranes.

In any embodiment, the colorimetric media can be one or more gas detection strips.

In any embodiment, the photodetector can detect an observable change in the colorimetric media.

In any embodiment, the photodetector can detect any one or more of a visual change in the colorimetric media, a change in an amount of ultraviolet light transmitted through or reflected from the colorimetric media, or a thermal change of the colorimetric media.

In any embodiment, the photodetector can detect a change in shape or size of the colorimetric media.

In any embodiment, the reaction detection and processing algorithm can be an image detection algorithm.

In any embodiment, the detected reaction can be a reaction of the colorimetric media and ammonia gas.

In any embodiment, the colorimetric media can be any one of: cube shaped, cylinder shaped, planar shaped, or spherical shaped.

In any embodiment, the colorimetric gas detector can be fluidly connected to a dialysate flow path.

In any embodiment, the colorimetric gas detector can include at least one colorimetric material reactable with a substance in a fluid.

In any embodiment, the substance in the fluid can be ammonium ions.

Any of the features disclosed as being part of the first aspect of the invention can be included in the first aspect of the invention, either alone or in combination.

The second aspect of the invention is drawn to a method. In any embodiment, the method can include flowing gas through the colorimetric gas detector of the first aspect of the invention; transmitting a light through the gas in the colorimetric gas detector; detecting light transmitted through the colorimetric media, reflected from the colorimetric media, or emitted by the colorimetric media; and determining the presence of at least one substance in the gas based on the detected light.

In any embodiment, the step of transmitting a light through the gas can include transmitting the light from a first side of the receiving slot; and the step of detecting light can include detecting light on a second side of the receiving slot.

In any embodiment, the step of determining the presence of at least one substance in the gas can include applying a reaction detection and processing algorithm to an image of the detected light.

In any embodiment, the step of detecting light can include detecting one or more of: a change in wavelength or intensity of visible light reflected from or transmitted through the colorimetric media, a change in wavelength or intensity of ultraviolet light reflected from or transmitted through colorimetric media, or a thermal change of the colorimetric media.

In any embodiment, the step of detecting light can include detecting one or more of: a change in shape of the colorimetric media, or a change in size of the colorimetric media.

In any embodiment, the method can include determining a concentration of the at least one substance in the gas based on the detected light.

In any embodiment, the at least one substance can include ammonia.

In any embodiment, the step of detecting light can include obtaining an image with a camera.

In any embodiment, the gas can be flowed from a degasser in a dialysate flow path to the colorimetric gas detector.

Any of the features disclosed as being part of the second aspect of the invention can be included in the second aspect of the invention, either alone or in combination.

The third aspect of the invention is drawn to a dialysate flow path. In any embodiment, the dialysate flow path can include a dialyzer, a sorbent cartridge, a dialysate pump, and a degasser; the degasser having a fluid inlet fluidly connected to the dialysate flow path, a fluid outlet fluidly connected to the dialysate flow path, and a gas removal line; a vacuum pump positioned on the gas removal line; and the colorimetric gas detector of the first aspect of the invention positioned on the gas removal line.

In any embodiment, the colorimetric gas detector can be positioned downstream of the degasser and upstream of the vacuum pump.

In any embodiment, the detected reaction can be reaction of the colorimetric media and ammonia gas.

Any of the features disclosed as being part of the third aspect of the invention can be included in the third aspect of the invention, either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

"Ammonia gas" is ammonia or $NH_3$ in a gaseous state.

The term "ammonium ions" refers to $NH_4^+$ ions dissolved in a fluid.

The terms "applying" or to "apply" mean to use or utilize.

A "colorimetric gas detector" is an apparatus that detects the presence of one or more substances in a gas based on an observable change in a colorimetric material in contact with the gas.

A "colorimetric media" is any material that can produce a detectable change based on one or more substances in contact with the material. The detectable change can include a visible change such as a change in color, optical transmittance, a change in emitted fluorescent light intensity or wavelength, or a change in the size or shape of the material.

The term "comprising" includes, but is not limited to, whatever follows the word "comprising." Use of the term indicates the listed elements are required or mandatory but that other elements are optional and may be present.

The term "concentration" refers to the amount of a substance in a given volume.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "cube shape" refers to a three-dimensional shape having 6 faces at meeting at right angles, the six faces having substantially the same dimensions.

The term "curved flow path" refers to any fluid path defining an arc of any degree. For example, a curved flow path can refer to fluid flowing in 180° path meaning the fluid flows in a first direction and then flows back in a reverse direction.

The term "cylinder shape" refers to a three-dimensional shape having a round top and sidewalls extending downwardly to a round base.

A "degasser" is a component capable of removing dissolved and undissolved gasses from fluids.

The terms "detecting," "detected," or "to detect" refer to determining a state or characteristic of a system.

The terms "determining" and "determine" refer to ascertaining a particular state of a system or variable(s).

A "dialysate flow path" is the pathway that dialysate will travel when used in normal operation for dialysis.

A "dialysate pump" is a device that causes the movement of fluids or gases through a dialysate flow path by applying suction or pressure.

The term "dialyzer" refers to a cartridge or container with two flow paths separated by semi-permeable membranes. One flow path is for blood and one flow path is for dialysate. The membranes can be in hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "electronic communication" refers to the ability to transmit electronic information between two components or systems.

The term "emitted" refers to light transmitted from any source.

A "fan" is a moveable component that increases the movement of a gas.

The terms "flow," "flowing," refer to a stream of gas, liquid, or combinations thereof moving, issuing, or circulating with a continual change of place among the constituent particles. As used in the phrase "flowing a gas," the term refers to a stream of gas.

A "fluid" is a liquid substance optionally having a combination of gas and liquid phases in the fluid. Notably, a liquid, as used, can therefore also have a mixture of gas and liquid phases of matter.

The term "fluid inlet" refers to a conduit or opening through which fluid or gas can enter a component or apparatus.

The term "fluid outlet" refers to a conduit or opening through which fluid or gas can exit a component or apparatus.

The term "fluidly connectable," "fluidly connect," "for fluid connection," "fluid communication," refer to the ability of providing for passing fluid or gas or mixtures thereof, from one point to another point. The two points can be within or between any one or more of compartments, modules, systems, components, and rechargers, all of any type. The connection can optionally be disconnected and then reconnected.

The term "gas" refers to a state of matter which expands to fill any space.

A "gas detection strip" is a thin material that produces an observable change when exposed to one or more gaseous substances.

A "gas removal line" is a line through which gases removed from a fluid by a degasser can be flowed out of the degasser.

An "image captured by a photodetector" refers to a digital representation of the visible light or fluorescent light detected by the photodetector.

An "image detection algorithm" is an algorithm that determines and identifies a portion of a digital image.

The term "intensity of light" refers to the amplitude of an electromagnetic wave.

The term "keypoints" refers to pixels or portions of an image that are used in an image recognition algorithm to recognize an object or portion of the image.

A "light source," "light emitter," "photo emitter," or the like, is any component capable of emitting light at any wavelength including visible, infrared, or ultraviolet light.

A "light guide" refers to a component that can transmit light in a defined path with total or near total internal reflectance using reflective surfaces of any type, size, position, and length.

The term "observable change" refers to any alteration in a substance that can be detected by a photodetector.

The term "obtaining an image" or to "obtain an image" refers to creating a digital representation of light transmitted through a lens of a camera.

The term "opposite" refers to a first side of a component or reference that faces or is positioned in a direction 180° away from a second side of the component.

A "photodetector," "camera," is a component capable of detecting light intensity, light composition, or both to result in data, such as an image, of the light detected. The terms "camera" and "photodetector" can also refer to any type of detector including an RGB detector or spectrophotometer.

The term "planar shaped" refers to a shape of an object that is substantially flat and extending in two dimensions.

The term "positioned" or "position" refers to a physical location of a component, feature, or structure.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The terms "quantitating" or to "quantitate" refer to determining a numerical value for a given parameter.

The terms "reacting," to "react," "reaction," or "reactable" refer to a chemical or physical change in a substance when contacted with at least one other substance.

A "reaction detection and processing algorithm" is a digitized method of determining an observable change to a colorimetric material based on light received by a photodetector.

The term "receiving slot" is a space within a sensor into which a second component can be placed.

The term "reflected" refers to light that contacts a material and then returns from the material.

A "sensing chamber" is a compartment or container within a component in which at least one characteristic of a substance within the sensing chamber can be determined.

A "sensing membrane" is a substrate with an embedded dye. The embedded dye can change color, change an amount or wavelength of transmitted light, and/or change an amount or wavelength of fluorescent light in response to a fluid characteristic, such as a particular concentration of a substance in a gaseous environment.

The term "sensor card" refers to a rigid and/or planar component having at least one sensing membrane or sensing material of any kind disposed on, inside or integral to the "sensor card." The sensing membrane or material can contact a fluid or gas, and produce a detectable change in response to a fluid characteristic of the fluid.

The term "shape" refers to the physical dimensions of a material.

A "side of the receiving slot" refers to a position relative to a receiving slot.

A "side of the sensing chamber" refers to a position relative to a sensing chamber.

The term "size" refers to the three dimensional volume or two dimensional area of a substance.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents that can remove solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

The term "spherical shape" refers to a three dimensional shape wherein each point on the outside of the object is approximately equal distance to the center.

The term "substance" refers to any material, solute, ion, gas, fluid, or compound.

The term "thermal change" refers to any change to the temperature of a substance.

The terms "transmitting light," to "transmit light" or "transmitted light" means to emit light onto or through a substance.

The term "transparent surface" refers to any material through which light can pass but through which fluids cannot pass.

The term "ultraviolet light" refers to electromagnetic radiation having a wavelength generally in a range from about 100 nm to 380 nm.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "vacuum pump" is a pump used to create negative pressure in a degasser and remove gas from the degasser.

The term "visual change" refers to any alteration in the wavelength or intensity of visible light transmitted through, reflected from, or emitted from a material.

The term "wavelength of light" refers to the distance between successive crests of an electromagnetic wave.

Colorimetric Gas Detector

Figure 1:
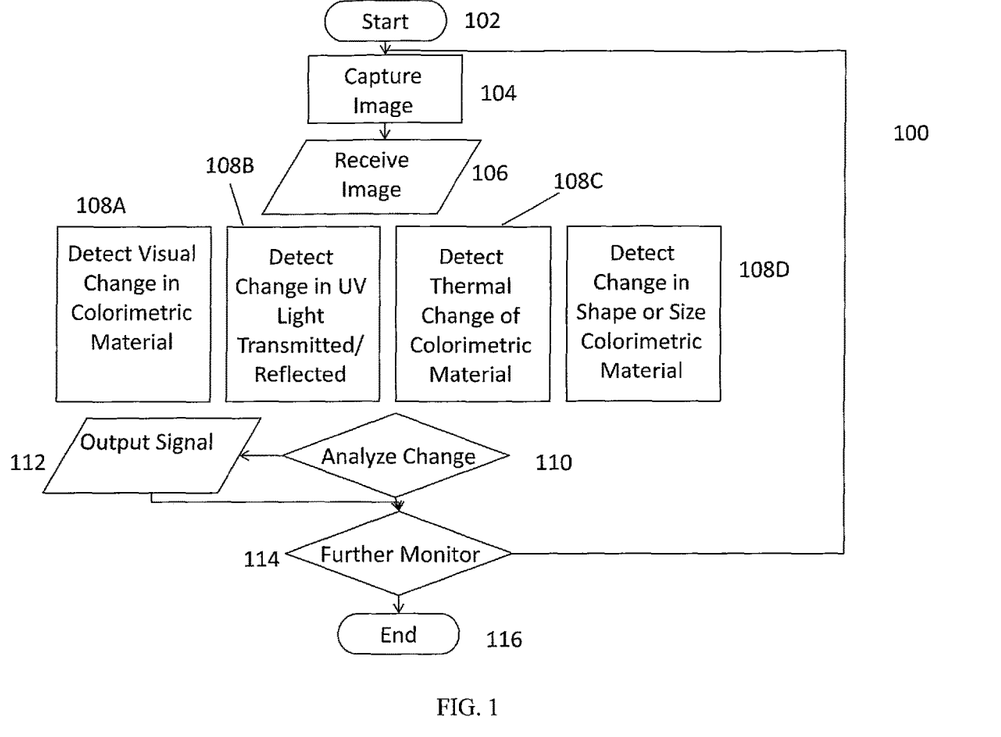
FIG. 1 is a flow chart illustrating a method for detection of one or more substances in a gas.

FIG. 1 discloses a colorimetric detection method 100 for detecting one or more substances in a gas. In operation 102, the method 100 may be initiated. A colorimetric gas detector can be fluidly connected to a fluid flow path or placed in a gaseous environment and fluid, gas or a mixture of fluid and gas may be introduced into a sensing chamber of the colorimetric gas detector, or may already flow through the sensing chamber. Fluid, gas, or a mixture of fluid or gas enters through a fluid inlet, into the sensing chamber and out through one or more fluid outlets. The fluid may be air or gas, a liquid or a mixture of liquid and gas phases. The colorimetric gas detector may be active or passive. In an active embodiment, one or more fans may be placed in the fluid inlet and/or the fluid outlets to enhance gas flow through the colorimetric gas detector, while in a passive embodiment gas may passively flow through the fluid inlet and/or outlets without a fan.

In operation 104, a photodetector or camera may obtain an image of a colorimetric media in a receiving slot of the sensing chamber. For example, the colorimetric media may be part of a sensor card. In one non-limiting example, the colorimetric media may take the form of one or more gas detection strips. In an alternative embodiment, the colorimetric media and/or its housing may be cube shaped, planar shaped, cylinder shaped, or spherical shaped. The colorimetric material may be reactable with a gas, or may be reactable with a gaseous substance dissolved in a fluid. The colorimetric material may also be reactable with solutes or ions dissolved in a fluid. Any combination of colorimetric materials can be used together. For example, one or more colorimetric material reactable with gas can be used with one or more colorimetric materials reactable with ions dissolved in a fluid. A light source can be positioned on one side of the receiving slot. The light source can transmit light through the receiving slot. A photodetector can be positioned on a second side of the receiving slot. The photodetector can receive the transmitted light from the light source. The captured image may be digitally stored in a processor in electronic communication with the photodetector.

In operation 106, the captured image may be transmitted to one or more processors. The one or more processors may execute instructions from a memory to execute an image recognition application to detect a reaction of the colorimetric media. The one or more processors and/or memory may be a part of the colorimetric gas detector or may be in electronic communication with the colorimetric gas detector. In general, specific substances in the gas will react with the colorimetric media resulting in a detectable reaction of the colorimetric media as captured by the photodetector.

In operation 108, the processor may quantitate a detected reaction of the colorimetric media from the image captured by the photodetector applying a reaction detection and processing algorithm. The reaction detection and processing algorithm can be any algorithm capable of determining an observable change in the colorimetric media based on the light transmitted through the sensing chamber of the colorimetric gas detector. The change in the colorimetric media can be a visual change in the colorimetric media, a change in an intensity or wavelength of ultraviolet light transmitted through or reflected from the colorimetric media, or a thermal change of the colorimetric media. The photodetector, such as a camera or a spectrophotometer, can determine the wavelength(s) and/or intensity of light passing through, emitted from, or reflected off of the colorimetric media. Any wavelength of light can be detected using any algorithm known in the art.

The reaction detection and processing algorithm may be an image detection algorithm. An image detection algorithm can include image by image, region by region, pixel by pixel comparison from one image to another. In image by image comparison, one or more entities in two or more images may be compared. In region by region comparison, the one or more processors may segment an image into regions. Similar regions of two or more images may be compared by the image processing application. In pixel by pixel comparison, similar pixels in two or more images may be compared by the image processing application. Keypoints of an image may be compared. Keypoints in an image can be determined. Keypoints can then be compared from one image to another image. Keypoints may identify size and shape of an object in the images. Color features may be compared using image by image, region by region, or pixel by pixel comparison. Each of two or more images can be analyzed using a color correlogram or a color histogram to identify color and/or contrast features in the images. The image captured by the photodetector can be compared to a baseline stored in the processor, or to a reference sensing region inside the colorimetric gas detector to quantitate the reaction between the colorimetric material and one or more substances in the fluid or gas.

The change in the colorimetric media can be correlated to one or more specific substances in the gas or fluid. For example, an ammonia sensitive dye embedded in a sensing membrane or in a gas detection strip can serve as the colorimetric media. The ammonia sensitive dye can be any dye capable of changing color in response to the ammonia level, including bromophenol-blue, bromocreosol green, thymol blue, methyl crystal purple, chlorophenol, free-base porphyrins, Tetraphenylporphyrin (H2TPP), and combinations thereof. Gaseous ammonia in the can react with the ammonia sensitive dye producing a reaction that changes the color of the ammonia sensitive dye. The change in color can be detected by the photodetector based on the wavelength and intensity of light transmitted through the sensing membrane or gas detection strip. Based on the resulting wavelength and intensity, the processor can quantitate the concentration of ammonia in the gas. Other substances that can produce detectable changes in a colorimetric media include hydrogen cyanide, hydrogen sulfide, phosphane, arsenic trihydride, or mercaptan. Any material that produces an observable change in a colorimetric media can be used as the colorimetric media in the colorimetric gas detector. The colorimetric material can also react with fluids or ions dissolved in fluids to produce a detectable change based on the concentration of the ions in the fluid.

The colorimetric media is not limited to color changes. Any observable change in a colorimetric media can be detected by the photodetector and quantitated by applying the reaction detection and processing algorithm. Certain materials, such as nitinol and hydrogels change shape in response to the temperature or moisture levels in the environment. The change in shape of the colorimetric media can be quantitated using an image recognition algorithm. Based on the detected shape of the colorimetric media, as determined by the light transmitted through or reflected from the colorimetric media, the presence or concentration of one or more substances can be determined by the processor.

Advantageously, colorimetric gas detector allows automation of detecting substances in a gaseous environment. The processor automatically determines the presence of, or concentration of, a substance in the gas without the need to manually make readings or correlate changes in a colorimetric material to substances that may be in the environment. The processor, photodetector, and light source can operate continuously to eliminate the need for an operator to detect substances that may be in a gaseous environment, thus providing a fast, accurate, and effective method of automatically determining the composition of gases. Further, the gas detection process can be conducted remotely, with the colorimetric gas detector transmitting the image captured by the photodetector to a remote processor for analysis, or by transmitting the results of the gas detection to a remote location, allowing gas detection without the need for a user to enter a potentially hazardous area. For example, a leak in a gas containment system may automatically be determined and an alert provided without the need for a user to initiate the process.

In the non-limiting example of operation 108A, a visual change in the colorimetric media may be detected in the captured image. For example, a change in color and/or contrast of all or part of the colorimetric media may be detected. In the non-limiting example of operation 108B, a change in ultraviolet light transmitted through the colorimetric media or reflected by the colorimetric media may be detected in the captured image. In the non-limiting example of operation 108C, a thermal change of the colorimetric media may be detected in the captured image, such as by detecting infrared radiation from the colorimetric media. In the non-limiting example of operation 108D, a change in the shape and/or size of the colorimetric media may be detected in the captured image.

In operation 110, a determination may be made whether the detected reaction of the colorimetric media matches one or more predetermined criterion for action being taken. For example, if a change in the color of the colorimetric media of a sensor card is detected, the processor may determine that a specific substance is present in a gas. In one non-limiting embodiment, the change in color of the colorimetric media may indicate the presence of ammonia gas. Based on the presence of ammonia in gas a warning may be output through an output interface. If during operation 110, a determination is made that the detected reaction of the colorimetric media matches one or more predetermined conditions, then the method 100 may proceed to operation 112. In operation 112, a signal may be output from the one or more processors to a system component. For example, if the colorimetric gas detector is in communication with a display, a signal displaying a warning regarding the presence of ammonia may be sent to the display. Alternatively, a signal displaying the concentration of one or more substances in the gas may be sent to the display. If during operation 112, a determination is made that the detected reaction of the colorimetric media does not match one or more predetermined conditions, then the method 100 may proceed to operation 114.

In operation 114, a determination may be made whether further monitoring using the colorimetric gas detector is desired. If during operation 114, a determination is made that further monitoring is desired, then the method 100 may return to operation 104 and a new image may be captured. Alternatively, the photodetector can continuously capture images, and no separate determination need be made. If during operation 114, a determination is made that further monitoring is not desired, then the method may return to operation 116 and end.

The colorimetric gas detector can detect substances in a gas, in a fluid, or in a mixture of fluid and gas. The colorimetric media can include one or more colorimetric materials reactable with a gas and one or more colorimetric materials reactable with solutes or ions dissolved in a fluid. For example, a first colorimetric material can react with ammonia gas, while a second colorimetric material can react with ammonium ions dissolved in a fluid. The colorimetric materials can be part of the same colorimetric media, such as a sensor card, or can be included in separate colorimetric materials. A single light source and photodetector can be included to detect substances in a gas and ions or solutes in a fluid, or separate light sources and/or photodetectors can be used.

Figure 2A:
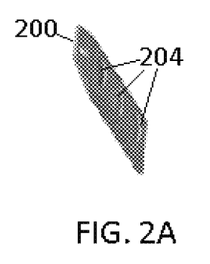
FIGS. 2A-D is a schematic representation of changes to a colorimetric media in response to a substance in a gas.
Figure 2B:
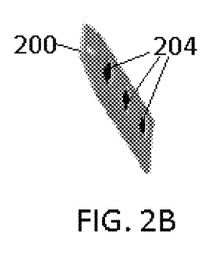

FIG. 2A is a schematic representation of a sensor card 200 including colorimetric material 202 within the sensor card 200. The colorimetric material 204 may be formed of any material that can react with a substance in a gas and produce an observable change in the colorimetric material. The colorimetric material 204 may be exposed through openings cutout of the sensor card. FIG. 2B is a schematic representation of the sensor card 200 of FIG. 2A, after exposure to a gas. In this non-limiting example, the exposure to the gas has caused the colorimetric material 204 to change color from grey to black. The sensor cards can include colorimetric materials or gas detection strips, each detecting the same or different substances in the gas. The sensor cards can also include a reference sensing region providing a non-reacting reference for comparison against the color or intensity of light transmitted through, reflected from, or emitted from the colorimetric material.

Figure 2C:
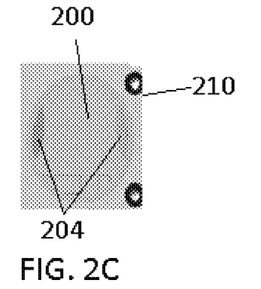
Figure 2D:
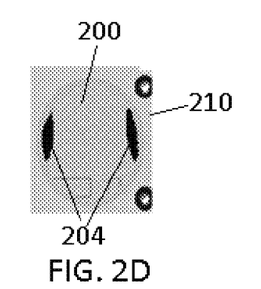

FIG. 2C is a schematic representation of a captured image 210 of the sensor card 200 of FIG. 2A before exposure to a gas. FIG. 2D is a schematic representation of a captured image 210 of the sensor card of FIG. 2B, after exposure to gas. The change in the colorimetric material from gray to black can be detected using the reaction detection and processing algorithm, and the reaction quantitated by the processor for determining the concentration or presence of a substance in the gas.

Figure 3A:
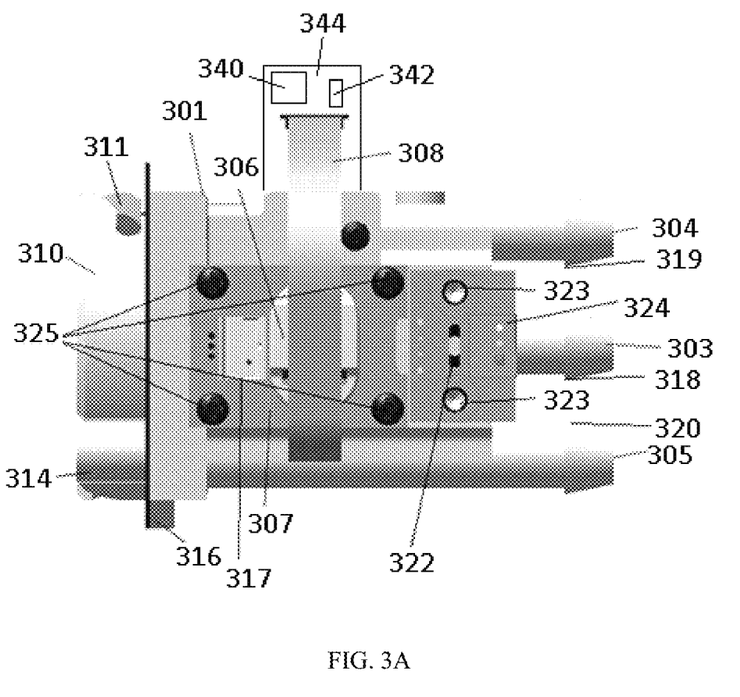
FIGS. 3A-F show a side, perspective, and top view of a colorimetric gas detector.
Figure 3B:
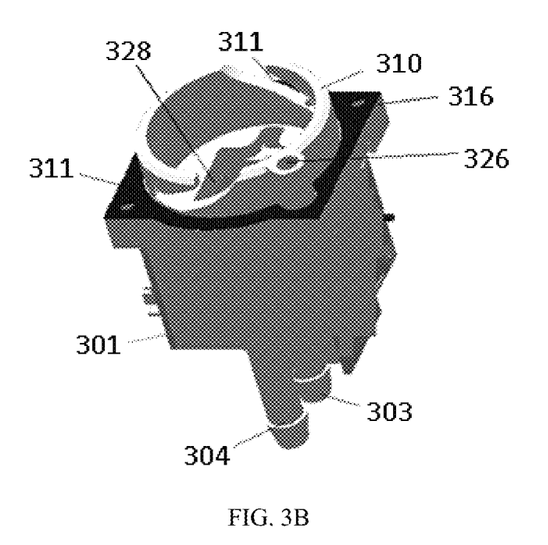
Figure 3C:
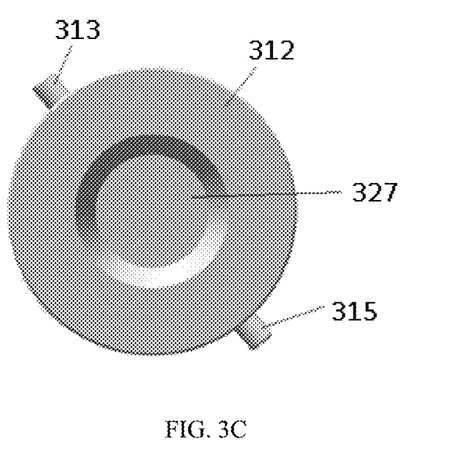
Figure 3D:
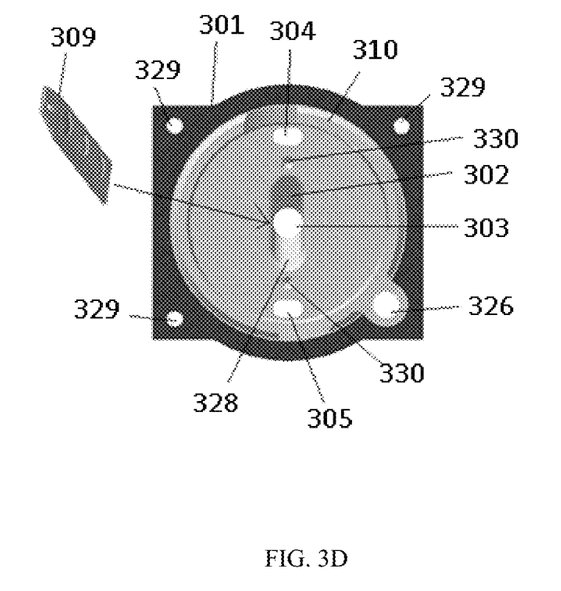
Figure 3E:
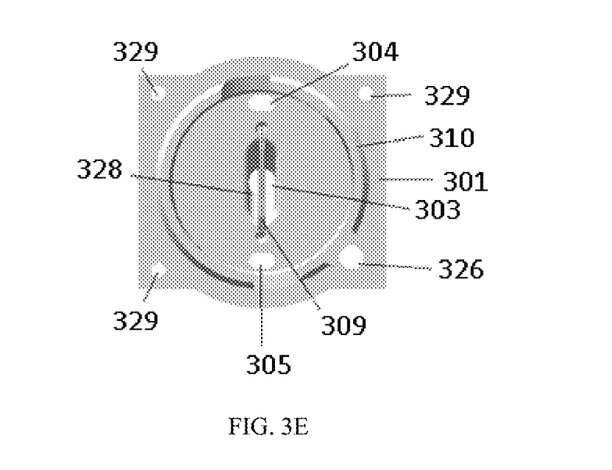
Figure 3F:
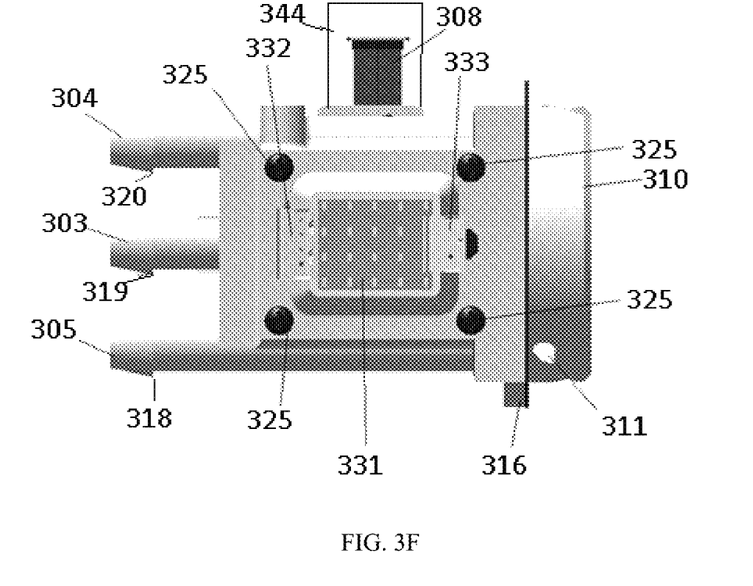

FIGS. 3A-F illustrate a non-limiting embodiment of colorimetric gas detector 301. FIG. 3A illustrates a side view of the colorimetric gas detector 301; FIG. 3B illustrates a perspective view of the colorimetric gas detector 301; FIG. 3C illustrates a receiving slot cover 312 for the colorimetric gas detector 301; FIG. 3D illustrates a cut-away portion of the colorimetric gas detector 301 at a specified depth and as sensor card 309 being inserted into a receiving slot 302 of the colorimetric gas detector 301; FIG. 3E illustrates a front view of the colorimetric gas detector 301 with the sensor card 309 inserted; and FIG. 3F illustrates a side view of the colorimetric gas detector 301.

As shown in FIG. 3D, the colorimetric gas detector 301 can optionally have a receiving slot 302 traversing a sensing chamber 328 along an axis. A removable sensor card 309, one or more gas detection strips, or any other colorimetric media, can be inserted into the receiving slot 102 as illustrated in FIGS. 1D and 1E to a specified depth of the colorimetric gas detector 301. The removable sensor card can include a colorimetric media 204 exposed through openings 206, as illustrated in FIG. 2, thereby creating a sensor. Indentations 330 on either side of the sensing chamber 328 at the depth of the colorimetric gas detector 301 in FIG. 3D, can receive an edge of the sensor card 309, to seat or fasten the sensor card 309 in place. At a higher depth of the colorimetric gas detector 301, a groove can be formed appurtenant to a sidewall of the sensing chamber 328 to receive a side edge of the sensor card 309. An edge of the sensor card 309 can be securely positioned in the sensing chamber 328 at a specified location or orientation with respect to a light source and/or photodetector. Alternatively, one or more grooves can be formed into the colorimetric gas detector 301 to receive an edge of the sensor card 309 to securely position the sensor card 309 at a specified location or orientation if the sensor card 309 has a width greater than any axis of the sensing chamber 328 as shown in FIG. 3E. The receiving slot can alternatively be formed to contain any size or shape of colorimetric media, including a cube shaped, cylinder shaped, planar shaped, or spherical shaped colorimetric media.

The sensing chamber 328 can optionally have a plurality of transparent windows on the sidewalls as shown in FIG. 3 to provide optical access to the sensor card 309. Holes 329 formed into the body of the colorimetric gas detector 301 can attach the colorimetric gas detector 301 to a console or system using screws or other fasteners as shown in FIG. 3D. The sensing chamber 328 extends longitudinally along a length of the receiving slot 302 of the colorimetric gas detector 301. The receiving slot 302 can extend beyond the sensing chamber 328 and terminate in a fastening mechanism to securely hold the sensor card 309, such as the indentation 330. The sensing chamber 328 can expose the colorimetric media to a flow of gas for detection. Notably, the sensing chamber 328 defines a volume such that a front side and a back side of the sensor card can be exposed to gas flow on both sides of the sensor card 309. The sampled gas can therefore simultaneously contact a first and second side (or front and back) of the sensor card to advantageously increase the surface area on which gas contacts colorimetric media in the sensor card resulting in improved sensing of the gas by the sensor card.

In an exemplary embodiment, the sensor card 309 can include one or more ammonia sensing membranes. Further, the ammonia sensing membranes can be low sensitivity or high sensitivity membranes or combinations thereof. The ammonia sensing membranes can change color, optical transmittance, or change emitted fluorescent light intensity or wavelength based on an ammonia level of a gas flowing through the sensing chamber 328. However, the sensor card is not limited to ammonia sensing membranes, and can include any colorimetric membrane producing a detectable change in response to a concentration or other parameter of a gas. In general, the colorimetric membrane can produce any visible change such as change in color or optical transmittance, or a change in emitted fluorescent light intensity or wavelength, wherein the visible change is detected by the photodetector or camera of the present invention.

The colorimetric media has a property reacting to a gas component that changes an optical parameter depending on the concentration of the component in the gas. The optical parameter can be any one of color, reflectivity, transitivity fluorescence, adsorption, size, shape, or any other parameter capable of being optically detected. In an embodiment, the colorimetric media changes color in relationship to changes in the gas concentration of the measured gas component. For example, the colorimetric media can change color in a first direction along a color spectrum as the concentration of the component in the gas increases, and along a second direction as the solute concentration of the component decreases. The color change of the membrane can be continuous and reversible in response to the component concentration. In the case of an ammonia sensing membrane, a dye can be embedded in a substrate, wherein the dye changes colors in response to an ammonia concentration of a gas.

Visual changes in the colorimetric media can be detected by the photodetector through one or more transparent surfaces positioned between a light source and the sensing chamber and the photodetector and sensing chamber. In FIGS. 3A-F, the transparent surfaces are clear windows positioned on the sidewall of the sensing chamber 328. However, the surface of the light source or sources and/or the lens of the photodetector can also or alternatively serve as the transparent surfaces.

In FIG. 3F, one non-limiting example of a light source is shown as LED array 331 connected to the system by electrical connector 317. The LED array 331 can transmit light onto a gas from a first side of the sensing chamber 328. The light can be directed through the one or more transparent surfaces in the sidewall of the sensing chamber 328. An arrangement of reflective surfaces can be used as a light guide to direct light from an LED array positioned on a side of the colorimetric gas detector 301 to be transmitted through the sensing chamber 128 and onto the photodetector or camera along any reflectance pathway. For example, a mirror arrangement can guide light to a camera or photodetector such that the camera or photodetector need not be in directly positioned opposite to the light source. The light guide can provide a reflectance pathway such that the camera or photodetector can be positioned in any convenient location to receive the reflected light. Similarly, the LEDs or any light source can rely on a light guide to direct light such that light sources can be conveniently positioned at any position, and need not be opposedly positioned to the camera or photodetector. In one embodiment, both the light source and the camera or photodetector transmit and receive light, respectively, using a light guide. The light source can be any source of light at any wavelength capable of shining light through the sensing chamber 328. In an embodiment, the LED provides white light; however, any color or wavelength of light can be used. In an embodiment, the light source provides uniform backlighting onto one side of the sensor card 309 such that a photodetector 306 (shown in FIG. 3A) positioned on an opposite side of the colorimetric gas detector 301 can detect visual changes in the colorimetric media between the photodetector and the light source via one or more transparent windows. The LED array 331 can be positioned at any part of the apparatus capable of providing uniform light through the sensing chamber 328, including direct and side-firing or side-emitting LEDs. In general, the transparent windows for the LED array 331 and photodetector 306 can be antipodal to each other. The photodetector 306 can be any appropriate camera, photodetector, spectrophotometer, or photosensor known to those of ordinary skill in the art. In performing a reaction detection and processing algorithm of a visual change in the colorimetric media in the sensing chamber, consideration of the photodetector's 306 angle of view and focal length can be considered relative to the dimensions of the sensing chamber including the optional receiving slot 302 and the light source. The angle of view describes the angular extent of a given scene that can be imaged by a camera. In an embodiment, a high power lens may be provided to detect slight changes in the colorimetric media. Alternatively, a magnifying sight, such as a magnifying lens, can be positioned between the photodetector and sensing chamber to magnify the view of the colorimetric media, enabling detection of small changes in the material. In an alternative embodiment, the reaction detection and processing algorithm can be tuned to detect changes of a particular magnitude. The image captured by the photodetector can be transmitted to a processor through wired or wireless communication for analysis. The processor can be integral to the colorimetric gas detector, or can be a remotely mounted from the sensing chamber and in electronic communication with the colorimetric gas detector. A single processor can receive data from any number of colorimetric gas detectors, allowing data to be analyzed from multiple sensors with a single processing unit. The processor can conduct a pixel scan of the image captured by the photodetector, and the density of the scan can be varied depending on the desired reaction detection. For example, a more-dense pixel scan will detect smaller changes.

The photodetector 306 can transmit the image or sensed output to one or more processors in electronic communication with the photodetector 306 for quantitating a detected visual change in the colorimetric media. In an embodiment, the one or more processors can determine, for example, an ammonia level of a gas. The camera or photodetector 306 can also detect fluorescent light emitted from the sensor card 309 or other colorimetric media. For detection of fluorescent light, an optical bandpass filter can be included in front of the photodetector to allow the emitted fluorescent light to pass to the photodetector while blocking any transmitted light from the LED array. The photodetector can detect any change in the light transmitted including the wavelength of light, the mean intensity of light, the variation in intensity of light, and the pixel location in an image produced by the photodetector.

Although illustrated as opposing the photodetector, the LED array 331 can be positioned anywhere on the colorimetric gas detector 301, including on any side of the colorimetric gas detector 301. A light guide can be included to allow light from an LED array positioned on a side of the colorimetric gas detector 301 to be transmitted through the sensor card and onto the photodetector along any reflectance pathway. For example, a mirror arrangement can guide light to a camera or photodetector such that the camera or photodetector need not be in directly positioned opposite to the light source. The light guide can provide a reflectance pathway such that the camera or photodetector can be positioned in any convenient location to receive the light. Similarly, the LEDs or any light source can rely on a light guide to direct light such that light sources can be conveniently positioned at any position, and need not be opposedly positioned to the camera or photodetector. In one embodiment, both the light source and the camera or photodetector transmit and receive light, respectively, using a light guide.

A grating light valve (not shown) having an adjustable diffraction grating can be included to control the intensity of light diffracted onto the photodetector 306. The diffraction grating can be a set of equally spaced, narrow, parallel grates. The grates can disperse the light at different wavelengths, so light intensity can be measured as a function of a particular wavelength. The transparent surfaces, such as clear windows, can be free from scratches that degrade the sensor performance. In one non-limiting embodiment, to reduce scratches to the clear windows, the windows can be solvent polished.

As shown in FIG. 3F, the photodetector 306 can transmit the image or other sensed output to one or more processors 340 in electronic communication with the photodetector 306 via electronic link 308. As with all features of the present application, intervening components (such as a circuit board 344) can be present between the processor 340 and the photodetector. The processor 340 may be in electronic communication with one or more memories 342. Memory 342 can be any machine-readable storage medium in communication with the processor 340 and can store instructions that when executed by the processor 340 perform the methods herein.

The processor 340 can determine the changes to colorimetric media in the sensing chamber 328 based on the sensed output. Electronics 307 of FIG. 3A can control the photodetector 306 and the light source. Although illustrated as having wired communication links between the photodetector, electronics, and processor, one of skill in the art will understand that any method of transmitting and receiving data can be used, including Bluetooth, Wi-Fi, or any other methods known in the art. The processor can receive data, and in particular the image captured by the photodetector, and determine the intensity of the pixels of a particular color in an image of the sensing membranes. A spectrophotometer, which measures the wavelength and intensity of the transmitted light, can also be used. Advantageously, a spectrophotometer can be more specific to a color of light detected. The processor can then detect changes to the colorimetric media using the reaction detection and processing algorithm. The processor 340 can be housed within, or positioned outside of, the colorimetric gas detector 301. The photodetector 306 can be operated under manual control or by a software application for controlling the exposure, gain and white balance.

As shown in FIG. 3A, gas can enter the colorimetric gas detector 301 through a fluid inlet 303 in fluid connection with the sensing chamber 328 and into the sensing chamber 328 of FIG. 3D. The gas can then exit the sensing chamber 328 through fluid outlets 304 and 305. The fluid outlets 304 and 305 and the fluid inlet 303 can be both positioned on the same side of the sensing chamber 328 to provide a curved fluid flow path such that gas enters through the fluid inlet 303 positioned in between fluid outlets 304 and 305 wherein gas then flows into a first end of the sensing chamber 328 and flows in a curved flow path and out a second end of the sensing chamber 328 and into the two fluid outlets 304 and 305 positioned on the same side as the sensing chamber 328. Conversely, the two fluid outlets 304 and 305 can be used as inlets to introduce gas into sensing chamber 328 along a curved flow path such that gas flows into and out of the fluid inlet 303. One of skill in the art will understand that one or more fluid inlets and outlets can be used. In a preferred embodiment, the two fluid outlets 304 and 305 advantageously improve the flow of the gas in the sensing chamber 328, which can improve colorimetric media change detection accuracy. Notch 318 on fluid inlet 303, notch 319 on outlet 304, and notch 320 on outlet 305 can provide secured fastening of the fluid inlet 303 and fluid outlets 304 and 305 to tubing as needed. Alternatively, the colorimetric gas detector 301 can be placed in a gaseous environment with gas flowing through the colorimetric gas detector 301, with no external tubing necessary. In FIG. 3C, the receiving slot 302 can include additional components to ensure that the detachable sensing chamber cover 312 fits tightly over the receiving slot 302 and does not move as gas is flowed into and through the sensing chamber 328. As illustrated in FIGS. 1A and 1B, the receiving slot 302 can have an extended portion 310 that will contact the sensing chamber cover 312 when closed. The extended portion 310 can include grooves 311 and 314 for receiving pins 313 and 315 when the sensing chamber cover 312 is placed over the sensing chamber 328. The pins 313 and 315 engage with the grooves 311 to ensure the sensing chamber cover 312 is properly placed and securely fastened on the colorimetric gas detector 301. An optional fan (not shown) can be positioned in the fluid inlet or fluid outlets of colorimetric gas detector 301 to provide active gas flow through the sensing chamber 328.

When used with a sensor card, the sensor card 309 can be fixed into a specified position and/or orientation inside the receiving slot 302 to resist any movement due to the flow of the gas. Any suitable fastener to fix the sensing chamber cover 312 to the colorimetric gas detector 301 is contemplated. Magnets can be placed within the sensing chamber cover 312 and the colorimetric gas detector 301. If the sensing chamber cover 312 is closed, the magnets can provide a means to determine if cover 312 is closed over the receiving slot 302 on the colorimetric gas detector 301.

As shown in FIG. 3F, overhang 316 can provide support for the receiving slot cover 312 when closed. In FIGS. 3D and 3E, opening 326 on extended portion 310 can provide for a fastener to be inserted through the receiving slot cover 312 to secure the receiving slot cover 312 onto the colorimetric gas detector 301. In FIG. 3C, an annular bevel 327 can be formed on the sensing chamber cover 312 to capture the sensor card 309 and hold the sensor card 309 securely locked in the colorimetric gas detector 301. Screws 325 fasten the electronics and photodetector 306 to the colorimetric gas detector 301. Alternative methods of securing components to the colorimetric gas detector 301 can be used, including adhesive, glue, bolts, or any other securing components known in the art. Holes 323 allow additional components and electronics to be added to the colorimetric gas detector 301. The accuracy of the sensor can also be improved by making the interior of the receiving slot non-reflective to prevent stray reflected light from interfering with the sensors. Similarly, any surface of the colorimetric material or sensor card can be non-reflective to improve accuracy and related light detection properties. The receiving slot, and/or sensor card can be constructed from a non-reflective material, or colored in a non-reflective color, such as black.

Figure 4:
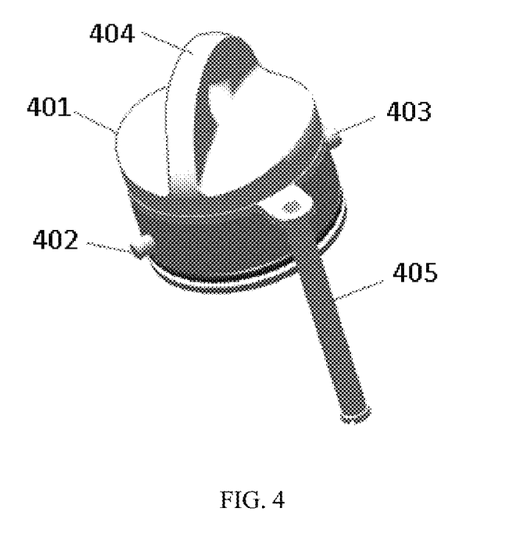
FIG. 4 shows a perspective view of a receiving slot cover for a colorimetric gas detector.

FIG. 4 illustrates a close-up view of a sensing chamber cover 401 of the colorimetric gas detector 301. As described, the sensing chamber cover 401 can include pins 402 and 403 to hold the sensing chamber cover 401 in place on the colorimetric gas detector 301 (FIG. 3A). The sensing chamber cover 401 can also include a handle 404 to facilitate twisting of the sensing chamber cover 401 for attachment and detachment of the sensing chamber cover 401 to the colorimetric gas detector 301. A sliding rod 405 can be included to secure the sensing chamber cover 401 when the sensing chamber cover is open on the colorimetric gas detector 301 and to prevent the cover from being removed during use. When used with a sensor card 309, the sensor card 309 can be fixed regarding the sensing chamber cover 401 to ensure that the sensor card does not move within the receiving slot 302 of FIG. 3D as gas flows past the sensor card. Fixing the sensor card within the colorimetric gas detector 301 provides the photodetector 306 (FIG. 3A) with a constant focal length, increasing the accuracy of the sensor. Additionally, a bevel 327 (FIG. 3C) can be included on an interior surface of the sensing chamber cover 401 for fixing the sensor card in place. The sensor card can be inserted into the bevel to lock the sensor card in a fixed position and to prevent insertion of the sensor card at a 180° rotation from the intended configuration. The bevel can only allow the sensor card to be inserted into the colorimetric gas detector in a single configuration. The bevel can be sized and shaped to conform to an edge of the sensor card, fixing the sensor card in position when placed into the bevel. The distance from the sensor card to the photodetector 306 can be any length, including between 15 and 20 mm. The lens of the photodetector can be configured with a focal length equal to the fixed distance between the photodetector 306 and sensor card 309.

The colorimetric gas detector can be used in any application where the presence or concentration of one or more gaseous substances is important. Non-limiting applications include freezer units, gas pipes, or any general space.

Figure 5:
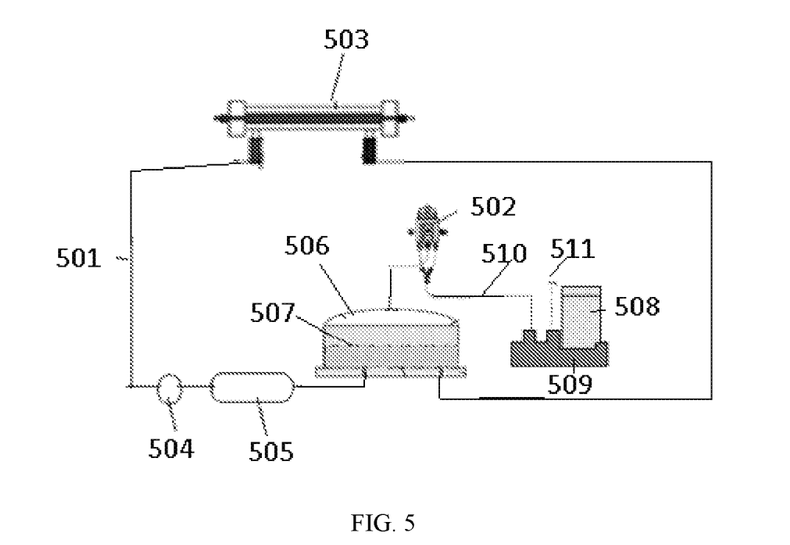
FIG. 5 is a dialysate flow path with a colorimetric gas detector.

One non-limiting application for the colorimetric gas detector is in dialysis. FIG. 5 illustrates a non-limiting embodiment of a dialysate flow path 501 including the colorimetric gas detector 502. One of skill in the art will understand that the dialysate flow path 501 illustrated in FIG. 5 is a simplified flow path, and that any number of additional components can be added as necessary. Dialysate pump 504 provides the driving force for flowing the dialysate through the dialysate flow path 501. Dialysate in the dialysate flow path 501 can pass through a dialyzer 503. Blood from a patient can be flowed through a blood flow path (not shown) and into the dialyzer 503. Solutes in the blood and dialysate can cross a semipermeable membrane in the dialyzer 503 to move from a high concentration side of the membrane to a low concentration side of the membrane. A principal waste product removed during dialysis is urea, which moves from the patient's blood into the dialysate in the dialyzer 503. The urea is removed from the dialysate in sorbent cartridge 505, which can contain urease to catalyze the conversion of urea to ammonium ions and carbonate ions. The ammonium ions can be removed by a cation exchange membrane or layer in the sorbent cartridge 505, as ammonia would be poisonous to pass back to the patient. Even though the ammonium ions are generally removed by the process, monitoring the presence of ammonium ions in dialysate fluid is desirable.

A degasser 506 can be included in the dialysate flow path 501 to remove dissolved and undissolved gases from the dialysate. If ammonium ions are present in the dialysate, ammonia gas will be present in the gas removed by the degasser 506. Dialysate enters the degasser 506, partially filling the degasser 506 with liquid. Dotted line 507 represents the interface between liquid and gas in the degasser 506. A vacuum pump 508 mounted on base 509 is connected to the degasser 506 through gas removal line 510. The vacuum pump 508 can assist removing dissolved gases from solution and removing gases from the degasser 506. Gases collected in the top portion of the degasser 506 are removed through gas removal line 510. The colorimetric gas detector 502 can be placed in gas removal line 510 to detect substances in the gases removed by the degasser 506. If ammonium ions are present in the dialysate downstream of sorbent cartridge 505, then ammonia gas will be present in gas removal line 510, which can be detected by the colorimetric gas detector 502. The colorimetric gas detector 502 can be positioned anywhere on the gas removal line 510. In a preferred embodiment, the colorimetric gas detector 502 is positioned downstream of the degasser 506 and upstream of the vacuum pump 508, as illustrated in FIG. 5.

One of skill in the art will understand that FIG. 5 is a simplified representative drawing of a dialysate flow path 501 with a degasser 506 and colorimetric gas detector 502. Additional components can be included in the dialysate flow path 501 and degasser 506. Further, although shown as a vacuum degasser 506, any type of degasser can be used, including degassers with a selective gas permeable membrane. The colorimetric gas detector 502 can be positioned to detect gases removed by any type of degasser in any type of dialysis system.

One skilled in the art will understand that various combinations and/or modifications and variations can be made in the described systems and methods depending upon the specific needs for operation. Features illustrated or described as being part of an aspect of the invention may be used in the aspect of the invention, either alone or in combination.

We claim:

1. A colorimetric gas detector, comprising:
a receiving slot for a colorimetric media reactable with a gas, the receiving slot positioned in a sensing chamber in fluid connection with at least one fluid inlet entering the sensing chamber and at least two fluid outlets exiting the sensing chamber; the at least one fluid inlet upstream of the receiving slot and each of the at least two fluid outlets downstream of the receiving slot, wherein each of the at least one fluid inlet and the at least two fluid outlets include a notch for secured fastening to a tubing;
a light source positioned one a first side of the receiving slot transmitting light through the receiving slot;
a photodetector positioned on a second side of the receiving slot receiving the transmitted light; and
a processor in electronic communication with the photodetector, the processor quantitating a detected reaction of the colorimetric media positioned in the receiving slot from an image captured by the photodetector using a reaction detection and processing algorithm.

2. The colorimetric gas detector of claim 1, further comprising a first transparent surface positioned between the light source and the receiving slot and a second transparent surface positioned between the photodetector and the receiving slot.

3. The colorimetric gas detector of claim 1, wherein the first side and second side of the receiving slot are on opposite sides of the colorimetric gas detector.

4. The colorimetric gas detector of claim 1, further comprising a fan positioned in the fluid inlet or in at least one of the at least two fluid outlets.

5. The colorimetric gas detector of claim 1, wherein the fluid inlet and the at least two fluid outlets are positioned on a first side of the sensing chamber.

6. The colorimetric gas detector of claim 1, wherein the receiving slot comprises a non-reflective interior surface.

7. The colorimetric gas of claim 1, further comprising a first light guide directing light from the light source to the first side of the receiving slot and a second light guide directing light received on the second side of the receiving slot directing light to the photodetector.

8. The colorimetric gas detector of claim 1, wherein the colorimetric media is positioned in a sensor card comprising one or more sensing membranes.

9. The colorimetric gas detector of claim 1, wherein the photodetector detects any one or more of a visual change in the colorimetric media, a change in an intensity or wavelength of ultraviolet light transmitted through or reflected from the colorimetric media, or a thermal change of the colorimetric media.

10. The colorimetric gas detector of claim 8, wherein the photodetector detects a change in shape or size of the colorimetric media.

11. The colorimetric gas detector of claim 1, wherein the reaction detection and processing algorithm is an image detection algorithm.

12. The colorimetric gas detector of claim 1, wherein the detected reaction is a reaction of the colorimetric media and ammonia gas.

13. The colorimetric gas detector of claim 1, wherein the colorimetric media is any one of: cube shaped, cylinder shaped, planar shaped, or spherical shaped.

14. The colorimetric gas detector of claim 1, wherein the colorimetric gas detector is fluidly connected to a dialysate flow path.

15. The colorimetric gas detector of claim 1, further comprising at least one colorimetric material reactable with a substance in a fluid.

16. The colorimetric gas detector of claim 15, wherein the substance in the fluid is ammonium ions.

17. The colorimetric gas detector of claim 1, further comprising a second fluid inlet entering the sensing chamber, the second fluid inlet upstream of the receiving slot.

18. A method, comprising the steps of:
flowing gas through the colorimetric gas detector of claim 1;
transmitting a light through the gas in the colorimetric gas detector;
detecting light transmitted through the colorimetric media, reflected from the colorimetric media, or emitted by the colorimetric media; and
determining the presence of at least one substance in the gas based on the detected light.

19. The method of claim 18, wherein the step of transmitting a light through the gas comprises transmitting a light from a first side of the receiving slot; and wherein the step of detecting light comprises detecting light on a second side of the receiving slot.

20. The method of claim 18, wherein the step of determining the presence of at least one substance in the gas comprises applying a reaction detection and processing algorithm to an image captured by the photodetector.

21. The method of claim 18, wherein the step of detecting light comprises detecting one or more of: a change in wavelength or intensity of visible light reflected from or transmitted through the colorimetric media, a change in wavelength or intensity of ultraviolet light reflected from or transmitted through colorimetric media, or a thermal change of the colorimetric media.

22. The method of claim 18, wherein the step of detecting light comprises detecting one or more of: a change in shape of the colorimetric media, or a change in size of the colorimetric media.

23. The method of claim 18, further comprising the step of determining a concentration of the at least one substance in the gas based on the detected light.

24. The method of claim 18, wherein the at least one substance includes ammonia.

25. The method of claim 18, wherein the step of detecting light comprises obtaining an image with a camera.

26. A dialysate flow path, comprising: a dialyzer, a sorbent cartridge, a dialysate pump, and a degasser; the degasser having a fluid inlet fluidly connected to the dialysate flow path, a fluid outlet fluidly connected to the dialysate flow path, and a gas removal line;
- a vacuum pump positioned on the gas removal line; and
- the colorimetric gas detector of claim 1 positioned on the gas removal line.

27. The dialysate flow path of claim 26, wherein the detected reaction is a reaction of the colorimetric media and ammonia gas.

* * * * *